US005643438A

United States Patent [19]

Hiebl et al.

[11] Patent Number: 5,643,438

[45] Date of Patent: Jul. 1, 1997

[54] PROCESS FOR THE PREPARATION OF SUBSTITUTED DIAMINO-DICARBOXYLIC ACID DERIVATIVES

[75] Inventors: Johann Hiebl; Franz Rovenszky, both of Linz, Austria

[73] Assignee: Hafslund Nycomed Pharma Aktiengesellschaft, Linz, Austria

[21] Appl. No.: 463,267

[22] Filed: Jun. 5, 1995

[30] Foreign Application Priority Data

Jul. 8, 1994 [AT] Austria .................................. 1348/94

[51] Int. Cl.$^6$ .................................................. C25B 3/00

[52] U.S. Cl. .......................... 205/435; 205/438; 205/441; 205/442; 560/157; 560/161; 560/169

[58] Field of Search .................................. 204/59 R, 72, 204/75, 76, 78, 79; 560/157, 161, 169

[56] References Cited

U.S. PATENT DOCUMENTS 3,879,271 4/1975 Nohe et al. .............................. 204/79

FOREIGN PATENT DOCUMENTS

WO9301206 1/1993 WIPO .

OTHER PUBLICATIONS

Nutt et al., "Useful Intermediates for Synthesis of Dicarba Analogues of Cystine Peptides: Selectively Protected α-Aminosuberic acid and α,α'-Diaminosuberic Acid of Defined Stereochemistry", *J. Org. Chem.,* 45 (no Month, 1980), pp. 3078–3080.

Schäfer: Angewandte Chemie 93, 978–1000, (no month 1981).

"Recent Contributions of Kolbe Electrolysis to Organic Synethsis", Electrochemistry IV, Springer-Verlag, (no month 1990,) pp. 92–95, E. Steckhan.

"Useful Intermediates for Synthesis of Dicarba Analogues of Cystine Peptides: Selectively Protected α-Aminosuberic Acid and α, α'-Diaminosuberic Acid of Defined Stereochemistry", J. Org. Chem. 1980 45, 3078–3080, Jan. 18, 1980, pp. 3078–3080, R. Nutt et al.

*Primary Examiner*—Kathryn L. Gorgos
*Assistant Examiner*—Edna Wong
*Attorney, Agent, or Firm*—Wenderoth, Lind & Ponack

[57] ABSTRACT

The invention relates to a new process for the preparation of substituted diaminodicarboxylic acid derivatives of the formula $$R^3O-\overset{\overset{O}{\|}}{C}-\underset{\underset{R^1-NH}{|}}{CH}-(CH_2)_n-\underset{\underset{R^2-NH}{|}}{CH}-\overset{\overset{O}{\|}}{C}-OR^3 \quad (I)$$

in a high yield by a modified Kolbe synthesis.

2 Claims, No Drawings

PROCESS FOR THE PREPARATION OF SUBSTITUTED DIAMINO-DICARBOXYLIC ACID DERIVATIVES

The invention relates to a new process for the preparation of substituted diaminodicarboxylic acid derivatives in a high yield by means of the Kolbe synthesis.

Substituted diaminodicarboxylic acid derivatives are valuable intermediate products in the synthesis of peptides.

In the synthesis which has been the most effective to date, for example, α-benzyl N-t-butyloxycarbonyl-glutamate is subjected to a Kolbe electrolysis. In this reaction, which proceeds under basic conditions, the anion of the protected amino acid is first oxidized and converted into a free radical intermediate, $CO_2$ being split off. This free radical can then react with a solvent proton or can in turn release a hydrogen atom to form a double bond, while reaction with a second free radical leads to the desired diaminodicarboxylic acid derivative. The decisive disadvantage of this method is a side reaction in which the reaction product can react with the alcohol of the solvent and can in this way be partly or completely transesterified. This process of course considerably reduces the yield of pure isolated product, which is a maximum of 20 % of theory, and also the product mixture formed can be purified only with particular difficulty and effort.

Surprisingly, it has been possible to find a process for the synthesis of diaminodicarboxylic acid derivatives which avoids the formation of transesterification products.

The invention therefore relates to a process for the preparation of substituted diaminodicarboxylic acid derivatives of the formula

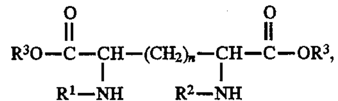

(I)

in which $R^1$ and $R^2$ in each case independently of one another are an optionally halogenated straight-chain, branched or cyclic alkyl radical having 1–10 C atoms or a radical

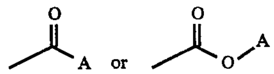

wherein A is an optionally halogenated straight-chain, branched or cyclic alkyl radical having 1–10 C atoms or a benzyl radical which is optionally mono- or polysubstituted by identical or different halogen, —$NO_2$, alkoxy or —CN substituents, or is 9-fluorenylmethyl and $R^3$ is a straight-chain or branched alkyl radical having 1–4 C atoms, the chirality centres in the molecules being determined by the starting materials used and it being possible for both to be in the L or both to be in the D or D,L or L,D configuration, and n is an integer from 2 to 8, by a Kolbe synthesis, wherein a protected amino acid derivative of the formula

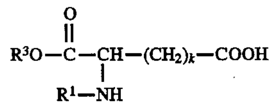

(II)

in which $R^1$ and $R^3$ have the abovementioned meaning and k is an integer, is dissolved with a protected amino acid derivative of the formula

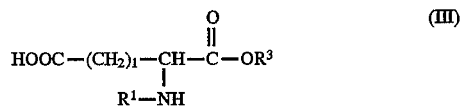

(III)

in which $R^1$ and $R^3$ have the abovementioned meaning and k is an integer, wherein k and 1 together give the number n, in a solvent $R^4OH$, wherein $R^4$ has the meaning of $R^3$, or a heterocyclic or aliphatic solvent containing at least one heteroatom or mixtures of such solvents, the solution is subjected to electrolysis on platinum gauze electrodes and, if appropriate, the product is hydrolysed with LiOH.

The advantage of this process is on the one hand the high yield of pure isolated product of at least 34% of theory, and on the other hand the fact that the purification effort can be reduced considerably owing to the lower content of by-products. This process is therefore capable of considerably reducing the preparation costs of secondary products, such as peptides, and compounds containing amino acids which do not occur naturally.

In the formulae I, II and III $R^1$ and $R^2$ are in each case an optionally halogenated straight-chain, branched or cyclic alkyl radical having 1–10 C atoms, for example a methyl, ethyl, n-propyl, i-propyl, n-butyl, i-butyl, t-butyl, pentyl, hexyl radical and the like, which can optionally be mono- or polyhalogenated.

$R^1$ and $R^2$ furthermore can be a radical

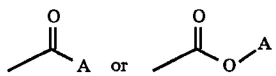

wherein A is a 9-fluorenylmethyl radical, or a benzyl radical which is optionally mono- or polysubstituted by identical or different halogen, $NO_2$, alkoxy or —CN substituents, for example a bromobenzyl, dibromobenzyl, chlorobenzyl, dichlorobenzyl, nitrobenzyl, methoxybenzyl or cyanobenzyl radical and the like.

$R^1$ and $R^2$ are preferably in each case a radical

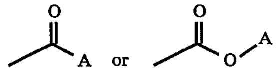

wherein A is a 9-fluorenylmethyl radical, an optionally substituted benzyl radical or a straight-chain or branched alkyl radical having 1–4 C atoms.

The radical $R^3$ is a straight-chain or branched alkyl radical having 1–4 C atoms, for example methyl, ethyl, n-propyl, i-propyl, n-butyl, i-butyl or t-butyl, preferably methyl, ethyl or i-propyl.

The compounds prepared by the present invention contain two asymmetric carbon atoms and may exist in racemic and optically active forms.

The chirality centres of the dicarboxylic acids are determined by the choice of starting materials used. They can either both be in the D or both be in the L or D,L or L,D configuration, for example N'—$R^1$—N"—$R^2$—2,7 —D,L—2,7-diaminosuberic acid di-$R^3$-esters when N-$R^1$-D-glutamic acid $R^3$-esters and N-$R^2$-L-glutamic acid $R^3$-esters are used.

The amino acid derivatives of the formulae II and III are dissolved in a solvent $R^4OH$ or a heterocyclic solvent, such as, for example, pyridine or dimethylformamide or acetonitrile, or mixtures of such solvents, wherein $R^4$ has the meaning of $R^3$, that is to say is, for example, methyl, ethyl, n-propyl, i-propyl, n-butyl or t-butyl, preferably methyl, ethyl or i-propyl.

A base, for example an alkali metal in $R^4$, for example sodium methoxide in methanol, or potassium ethoxide in ethanol, is added to the solution in the electrolysis cell.

Electrolysis is then carried out on platinum gauze electrodes, while cooling, the temperature being preferably kept at 18–25° C. The current strength during the electrolysis is about 5–15 A with a voltage of 60–120 V applied, and furthermore depends on the geometry of the electrode used.

The electrolysis operation is ended as soon as no further starting material can be detected in the electrolysis solution.

The electrolysis solution is then concentrated, if appropriate under low pressure, the residue is taken up in a suitable solvent, for example ethyl acetate, and this solution is washed successively with dilute acid, for example dilute hydrochloric acid, a saturated salt solution, for example a saturated sodium bicarbonate solution, and saturated sodium chloride solution. The solution is then dried with a suitable drying agent, for example sodium sulphate or magnesium sulphate, filtered and concentrated again, if appropriate under reduced pressure.

The residue is purified by chromatography, for example over silica gel, which is possible with comparatively little effort because of the low content of by-products. Compared with a previous process in which $R^3$ and $R^4$ were not identical, the reaction proceeds in a yield of up to 35% of theory, in contrast to 10–15% previously.

EXAMPLE 1

47.40 g (181 mmol) of α-t-methyl N-t-butyloxycarbonylglutamate were dissolved in 240 ml of MeOH and 80 ml of pyridine by swirling. The reaction solution was transferred to the electrolysis cell with cylindrically arranged platinum gauze electrodes. The dissolution vessel was rinsed with MeOH and the electrolysis cell was topped up with MeOH until the two electrodes were completely immersed.

0.8 ml of $NaOCH_3$(30% strength in MeOH) was now added and the reaction solution was cooled to 15° C. The reaction temperature was kept at between +18° C. and +24° C. by temperature regulation or by regulation of the current strength and voltage (5–15 A, 60–120 V).

The course of the reaction was monitored by means of TLC. When the reaction was complete, the reaction solution was evaporated on a rotary evaporator at 40 ° C.

The residue of the Kolbe synthesis was dissolved in 250 ml of ethyl acetate and the solution was washed first with dilute HCl solution (75 ml of concentrated HCl topped up to 200 ml with $H_2$ O), then with 200 ml of saturated $NaHCO_3$ and finally with 200 ml portions of saturated NaCl until the aqueous phase was neutral.

The organic phase was dried with $Na_2$ $SO_4$ and filtered and the filtrate was evaporated. Evaporation residue: 37.93 g.

The evaporation residue was filtered over silica gel and then separated by means of column chromatography.

The product-containing fractions were concentrated and 13.69 g of colourless crystals were obtained from the oily residue (24.08 g) from 100 ml of petroleum ether:cyclohexane =3:1.

Yield: 13.69 g of pure dimethyl bis-N',N"-benzyloxycarbonyl-2,7-diaminosuberate (35 % of theory), melting point 65–68° C.

$^{13}$ C($CDCl_3$, 100 MHz): 24.86(2$CH_2$), 28.30(($CH_3$) $_3$C), 32.53(2$CH_2$), 52.17(2OMe), 53.29(2CH), 79.87(2($CH_3$)$_3$C), 155.31 (2carbamate-CO), 173.20 (2ester-CO).

EXAMPLE 2

1.5 g (1.16 mmol) of dimethyl bis-N',N"-benzyloxycarbonyl-2,7-diaminosuberate were dissolved in a solution of 1.5 ml of water and 3 ml of MeOH. 1.45 ml (2.90 mmol, 1.25 equivalents) of a 2 N LiOH solution in water were added to this solution. A clear solution was formed from the slightly cloudy solution by careful addition of about 1 ml of MeOH. The reaction solution was stirred at room temperature and then concentrated to 3 ml on a Rotavapor, and the pH of the solution was brought to 2–3 with 5% strength $KHSO_4$ solution. The acid solution was extracted with chloroform and the organic phase was dried with $Na_2SO_4$, filtered and concentrated. 0.555 g of crude product, which was recrystallized from acetonitrile, was obtained.

Yield: 0.324 g (80%). Analysis by chiral capillary electrophoresis shows that no racemization is detectable.

The following compounds were synthesized analogously to Examples 1 and 2:

Di -Boc -D, D-SUB-di -OMe Yield: 1.15 g, (35 % of theory), melting point: 42–47° C. $^1$H NMR (400 MHz, $CDCl_3$) δ4.99(s, 2 H, 2 NH), 4.27(s, 2 H, 2 CH), 3.73(s, 6 H, 2OMe), 1.76 and 1.60(m, 2 H), 1.44(s, 18 H), 135(m, 4 H). $^{13}$ C NMR (100 MHz, $CDCl_3$) δ173.2, 155.3, 79.9, 53.3, 52.2, 32.5, 28.3, 24.9.

Di -Boc -D, D-SUB

Yield: 0.37 g (79% of theory), melting point: 152–154° C. $^1$ H NMR (400 MHz, MeOH-$d_3$) δ4.12(s, 2 H, 2 CH), 1.82 and 1.70(m, 2 H), 1.48(s, 18 H, 2 C($CH_3$)$_3$), 1.45(m, 4 H, 2 $CH_2$), $^{13}$ C NMR (100 MHZ, DMSO-$d_6$) δ176.5, 158.1, 80.8, 55.1, 33.0, 29.0, 26.8.

Di -BOC-L, L-SUB-di -OEt

Yield: 7.29 g (33.6% of theory), slightly yellowish oil.

$^1$ H NMR (400 MHz, $CDCl_3$) δ5.00(br s, 1 H, NH), 4.26(br s, 1 H, CH) 4.19(q, 2 H, $OCH_2$ $CH_3$), 2.46(m, 2 H), 1.78 and 1.60(m, 2 H), 1.44(s, 18 H), 1.35(m, 4 H), 1.28(t, 3 H, $OCH_2$ $CH_3$).

$^{13}$ CNMR (100 MHz, $CDCl_3$) δ172.4, 155.0, 79.4, 60.9, 53.1, 32.3, 28.0, 24.6, 143.9.

Di-BOC-L, L-SUB

Yield: 3.7 g (84 %), melting point: 150–153° C.

| C, H, N analysis: | C | H | N |
|---|---|---|---|
| Calculated: | 53.4 | 7.97 | 6.93 |
| Found: | 53.2 | 8.1 | 6.8 |

The abbreviations used above have the following meanings:

Boc: t-butyloxycarbonyl

SUB: 2,7-diaminosuberic acid

Me: Methyl

Et: Ethyl

What we claim is:

1. Process for the production of substituted diaminodicarboxylic acid derivatives of the formula

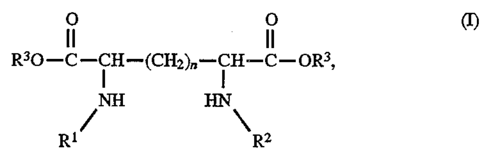

(I)

in which $R^1$ and $R^2$ in each case independently of one another are an optionally halogenated straight-chain, branched or cyclic alkyl radical having 1 to 10 carbon atoms or a radical

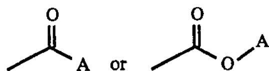

wherein A is an optionally halogenated straight-chain, branched or cyclic alkyl radical having 1 to 10 carbon atoms or a benzyl radical which is optionally mono- or polysubstituted by identical or different halogen, —$NO_2$, alkoxy or —CN substituents, or is 9-fluorenylmethyl, and $R_3$ is a straight-chain or branched alkyl radical having 1 to 4 carbon atoms and n is an integer from 2 to 8, by Kolbe synthesis, wherein a protected amino acid derivative of the formula

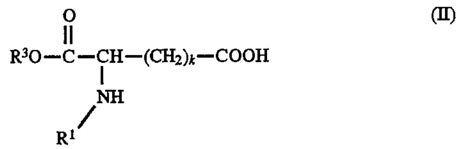

in which $R^1$ and $R^3$ have the above mentioned meaning and k is an integer, and a protected amino acid derivative of the formula

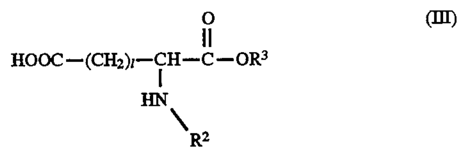

in which $R^2$ and $R^3$ have the above mentioned meaning and 1 is an integer;

k+1=n;

are dissolved in a solvent $R^4$ OH, wherein $R^4$ has the meaning of $R_3$, or a mixture of $R^4$ OH and a heterocyclic or aliphatic solvent containing at least one hetero atom, and the resulting solution is subjected to electrolysis on platinum gauze electrodes.

2. Process for the preparation of substituted diaminodicarboxylic acid derivatives of the formula I according to claim 3, in which $R^1$ and $R^2$ are each a radical

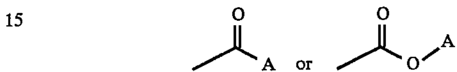

wherein A is an optionally halogenated straight-chain, branched or cyclic alkyl radical having 1 to 10 carbon atoms or a benzyl radical, which is optionally substituted by halogen, —$NO_2$, alkoxy or —CN, or is 9-fluorenylmethyl and $R^3$ is a straight-chain or branched alkyl radical having 1 to 4 carbon atoms, the reaction taking place in a solvent mixture of $R^4$ OH and pyridine or $R^4$ OH and dimethylformamide or $R^4$ OH and acetonitrile, wherein $R^3$ and $R^4$ are identical, where the yield of reaction product of formula I is 1.5 to 3 times the yield when $R^3$ and $R^4$ are not identical.

* * * * *